(12) United States Patent
Georgeson et al.

(10) Patent No.: US 9,372,177 B2
(45) Date of Patent: Jun. 21, 2016

(54) METHOD AND SYSTEM FOR DETECTING EXPOSURE OF COMPOSITES TO HIGH-TEMPERATURE

(71) Applicant: The Boeing Company, Chicago, IL (US)

(72) Inventors: Gary E. Georgeson, Federal Way, WA (US); Megan N. Watson, Kent, WA (US); Morteza Safai, Newcastle, WA (US)

(73) Assignee: THE BOEING COMPANY, Chicago, IL (US)

( * ) Notice: Subject to any disclaimer, the term of this patent is extended or adjusted under 35 U.S.C. 154(b) by 162 days.

(21) Appl. No.: 13/840,980

(22) Filed: Mar. 15, 2013

(65) Prior Publication Data
US 2014/0273240 A1    Sep. 18, 2014

(51) Int. Cl.
| | |
|---|---|
| *G01N 21/88* | (2006.01) |
| *G01N 31/22* | (2006.01) |
| *C09D 5/26* | (2006.01) |
| *G01K 11/20* | (2006.01) |
| *G01N 21/91* | (2006.01) |
| *G01N 21/84* | (2006.01) |

(52) U.S. Cl.
CPC ............. *G01N 31/229* (2013.01); *C09D 5/26* (2013.01); *G01K 11/20* (2013.01); *G01N 21/91* (2013.01); *G01N 2021/8472* (2013.01)

(58) Field of Classification Search
CPC .................................................... G01N 31/229
USPC ............................................ 422/82.08; 436/7
See application file for complete search history.

(56) References Cited

U.S. PATENT DOCUMENTS

| | | | |
|---|---|---|---|
| 2,417,384 A | 3/1947 | Switzer | |
| 2,712,507 A | 7/1955 | Green | |
| 2,889,799 A | 6/1959 | Korpman | |
| 3,078,182 A | 2/1963 | Crone, Jr. et al. | |
| 3,239,366 A | 3/1966 | Miller et al. | |
| 3,243,303 A | 3/1966 | Johnson | |
| 3,667,916 A | 6/1972 | Silva et al. | |
| 3,744,295 A * | 7/1973 | Allinikov | 427/8 |
| 4,105,583 A * | 8/1978 | Glover et al. | 436/7 |
| 4,188,437 A | 2/1980 | Rohowetz | |

(Continued)

FOREIGN PATENT DOCUMENTS

| | | |
|---|---|---|
| EP | 0538580 | 4/1993 |
| GB | 2194062 | 2/1988 |

(Continued)

OTHER PUBLICATIONS

Nevadunsky, J. J. et al, Journal of Composite Materials 1975, 9, 394-408.*

(Continued)

*Primary Examiner* — Arlen Soderquist
(74) *Attorney, Agent, or Firm* — Thompson Hine LLP (57) ABSTRACT

A method of detecting high-temperature exposure of a composite may include applying a composition comprising an adduct suitable for detecting heat and/or mechanical stress in a composite, wherein the adduct reverts to first and second adduct components after exposure of the composition to a temperature of from about 190° C. to about 260° C. to a surface of the composite; exposing the surface to which the composition has been applied to ultraviolet light; and measuring fluorescence of the composition.

19 Claims, 6 Drawing Sheets

(56) References Cited

U.S. PATENT DOCUMENTS

| | | | |
|---|---|---|---|
| 4,212,153 A | | 7/1980 | Kydonieus et al. |
| 4,273,674 A | * | 6/1981 | Ligon et al. .................. 436/7 |
| 4,292,916 A | | 10/1981 | Bradley et al. |
| 4,344,909 A | * | 8/1982 | De Blauwe .................. 264/230 |
| 4,470,122 A | * | 9/1984 | Sarr .................. 702/150 |
| 4,661,305 A | * | 4/1987 | Carlomagno .................. 264/132 |
| 4,675,161 A | | 6/1987 | Hashimoto et al. |
| 4,677,473 A | * | 6/1987 | Okamoto et al. .................. 348/126 |
| 4,717,674 A | * | 1/1988 | Sung .................. 436/85 |
| 4,834,909 A | * | 5/1989 | Nagel .................. 252/408.1 |
| 4,958,853 A | | 9/1990 | Doty |
| 4,963,415 A | * | 10/1990 | Carlson et al. .................. 428/199 |
| 5,100,802 A | | 3/1992 | Mickols .................. 436/34 |
| 5,282,017 A | * | 1/1994 | Kasindorf et al. .................. 356/446 |
| 5,308,887 A | | 5/1994 | Ko et al. |
| 5,384,079 A | * | 1/1995 | Bur et al. .................. 264/21 |
| 5,424,841 A | * | 6/1995 | Van Gelder et al. .................. 356/417 |
| 5,425,824 A | * | 6/1995 | Marwick .................. 156/64 |
| 5,438,879 A | | 8/1995 | Reda |
| 5,539,013 A | * | 7/1996 | Eckberg et al. .................. 522/75 |
| 5,756,356 A | | 5/1998 | Yanagi et al. |
| 5,780,857 A | * | 7/1998 | Harju et al. .................. 250/458.1 |
| 5,790,718 A | | 8/1998 | Tenner et al. |
| 5,828,460 A | * | 10/1998 | Lucovsky et al. .................. 356/446 |
| 5,854,684 A | * | 12/1998 | Stabile et al. .................. 356/440 |
| H1843 H | * | 3/2000 | Bur et al. .................. 250/458.1 |
| 6,486,319 B1 | * | 11/2002 | Bohm et al. .................. 546/38 |
| 7,050,535 B2 | * | 5/2006 | Georgeson et al. .................. 378/57 |
| 7,246,570 B2 | | 7/2007 | Weng et al. |
| 7,514,262 B2 | | 4/2009 | Ribi |
| 7,517,146 B2 | | 4/2009 | Smith et al. |
| 7,647,809 B1 | | 1/2010 | Cooney |
| 7,682,830 B2 | | 3/2010 | Prusik et al. |
| 7,712,431 B2 | * | 5/2010 | Roche .................. 116/216 |
| 8,083,423 B2 | | 12/2011 | Roth et al. |
| 8,432,537 B2 | | 4/2013 | Lam et al. |
| 8,691,383 B2 | | 4/2014 | Georgeson et al. |
| 9,085,052 B1 | | 7/2015 | Georgeson |
| 2002/0000128 A1 | | 1/2002 | Williams |
| 2002/0154396 A1 | * | 10/2002 | Overbeck .................. 359/368 |
| 2004/0121071 A1 | * | 6/2004 | Loyd et al. .................. 427/212 |
| 2005/0018898 A1 | * | 1/2005 | White et al. .................. 382/145 |
| 2005/0109984 A1 | * | 5/2005 | Potyrailo et al. .................. 252/299.01 |
| 2006/0056585 A1 | * | 3/2006 | Georgeson et al. .................. 378/57 |
| 2006/0116442 A1 | * | 6/2006 | Gallo et al. .................. 523/200 |
| 2006/0157195 A1 | | 7/2006 | Laurence et al. |
| 2008/0209825 A1 | * | 9/2008 | Smith .................. 52/169.14 |
| 2008/0223152 A1 | | 9/2008 | Georgeson et al. |
| 2009/0036304 A1 | | 2/2009 | Misner et al. |
| 2010/0196637 A1 | | 8/2010 | Lippert et al. |
| 2011/0008587 A1 | | 1/2011 | Ruskin |
| 2011/0123712 A1 | | 5/2011 | Becker, IV et al. |
| 2012/0275968 A1 | * | 11/2012 | Puntambekar .................. 422/400 |
| 2013/0122594 A1 | * | 5/2013 | Hughes et al. .................. 436/7 |
| 2014/0273240 A1 | | 9/2014 | Georgeson et al. |
| 2015/0321496 A1 | | 11/2015 | Clayton et al. |

FOREIGN PATENT DOCUMENTS

| | | |
|---|---|---|
| JP | 06-313738 | 11/1994 |
| WO | 0072055 | 11/2000 |

OTHER PUBLICATIONS

Richards, R. F. et al, Fire Safety Journal 1997, 28, 351-378.*
Stefani, F. D. et al, Chemistry of Materials 2006, 18, 6115-6120.*
Lempereur, C. et al, Measurement Science and Technology 2008, 19, 105501, 11 pages.*
Khatibi, A. A. et al, Polymer Composites 2008, 29, 798-803.*
Feraboli, P. et al, Composites: Part A 2009, 40, 954-967.*
Edwards, G. R., Proceeding of the 2nd International Conference on Testing, Evaluation and Quality Control of Composites-TEQC 87 1987 Herriot, J., editor, Butterworths, London, England, 3-10.*
Chen, Z. et al, Experimental Techniques 2000, 24, 29-32.*
Coleto, J, et al, IAC-06-C2[1].5.03 2006, 12 pages.*
Howie, T. et al., "Detection of Thermal Damage of CFRP Using Fluorescent Thermal Damage Probes," SAMPE Technical Conference, Charleston, SC (Oct. 23, 2012).
Extended European Search Report and Search Opinion, European Application No. 14158434.2 (Dec. 11, 2014).
Fisher, W.G. et al., "Nondestructive Inspection of Graphite-Epoxy Composites for Heat Damage Using Laser-Induced Fluorescence," Applied Spectroscopy, vol. 49, No. 9, pp. 1225-1231 (Sep. 1995).
Seeboth, A. et al., "Thermochromic Polymer Materials," Chinese Journal of Polymer Science, vol. 25, pp. 129-135 (Jan. 2007).
"Impact Indicator Paint for Composites"; Air Force SBIR/STTR Innovation, SBIR Topic #AF04-133, RX2008-127; 2 pages (2008).
PCT, "International Search Report and Written Opinion", International Application No. PCT/US2012/023127, 12 pages (May 18, 2012).
Van Keuren, Edward et al., "Three-dimensional thermal imaging using two-photon microscopy"; Institute of Physics Publishing, 37; pp. 2938-2943 (2004).
Wu, Wen-Chung et al., "Enhancement of Aggregation-Induced Emission in Dye-Encapsulating Polymeric Micelles for Bioimaging", Advanced Functional Materials, 20, pp. 1413-1423 (2010).
Yang, Jun et al., "Excimer Formation in Uniaxially Stretched Polymer Films", Journal of AppliedPolymer Science, vol. 82 (2001), pp. 2347-2351 (Sep. 15, 2000).
Toivola, Ryan E. et al., "Stress Sensitive Fluorescent Dyes for Damage Detection in Aerospace Primers & Coatings", University of Washington Materials Science & Engineering, Seattle, WA, 17 pages.

* cited by examiner

METHOD AND SYSTEM FOR DETECTING EXPOSURE OF COMPOSITES TO HIGH-TEMPERATURE

FIELD

The present disclosure relates to composites, and more particularly, to methods and systems for detecting exposure of composites to high temperatures.

BACKGROUND

Many different techniques have been utilized to try to evaluate and detect incipient thermal damage to CFRP parts including FTIR, laser-induced fluorescence, Raman spectroscopy, and NMR. While many of the techniques have been shown capable of detecting incipient thermal damage most of them are not viable options for inspection of parts in service. Currently the most prominent means of detecting incipient thermal damage for in service inspection is diffuse reflectance infrared Fourier transform spectroscopy (DRIFT). DRIFT spectroscopy is capable of detecting and providing quantitative information changes to the functional groups of the matrix which are affected as the matrix thermally degrades. Changes in the carbonyl and phenol bands of the FTIR spectrum were found to correlate fairly well with changes to mechanical properties such as ILSS and were sensitive to early signs of oxidation before significant strength loss occurred. One of the main issues with DRIFT spectroscopy though is that it has a very small spot size relative to the size of many parts so it is not a very efficient wide-area technique. As a result it can be difficult to locate and evaluate thermal damage sites on large CFRP parts if the damage site is not already known. Another method that showed promise as a wide-area inspection technique for incipient thermal damage was laser-induced fluorescence (LIF). LIF works by using a laser excitation source to excite the autofluorescence of the matrix. It has been found that both the intensity and the wavelength at the max intensity $\lambda_{max}$, change as a result of thermal damage, however only the $\lambda_{max}$ was shown to correlate directly to changes in mechanical properties such as flexural strength. Both DRIFT and LIF are only surface sensitive techniques however, so considerable testing needs to be done to determine how well they apply to bulk materials. Thermo-elastic characterization has been shown as possible method for detecting volumetric thermal degradation. Thermo-elastic characterization works by using an acoustic horn to generate a high amplitude acoustic wave that generates heat as it passes through the material and an IR camera is used to measure the change in temperature. Potential thermal damage can be observed by changes in the slope of temperature over the amplitude of the wave ($\Delta T/\Delta A$). Thermo-elastic characterization has also shown good potential for finding incipient thermal damage however, there is very little literature available so it is difficult to evaluate its applicability to in field use.

A common issue with all of these inspection methods except for LIF is that while they are capable of detecting thermal damage on a sample, they are not very efficient for inspecting large parts if the damage location is not known. Since incipient thermal damage of CFRP can be very difficult to locate visually this can be a problem for inspecting large aircraft parts for thermal damage.

To be an efficient and reliable tool to detect the thermal damage of CFRP, the probing molecule is required to respond to the proper temperature window. From the molecular level point of view, dynamic covalent chemistry and non-covalent intermolecular interactions, triggered at elevated temperatures, generally offer intriguing opportunities in inducing fluorescence change. Typically, non-covalent interactions are generally more susceptible to the external environmental factors, and thus kinetically labile. In this sense, thermally induced covalent chemistry is the more suitable and reliable approach to design efficient fluorescent molecular probes for detection and evaluation of the thermal damage on a CFRP samples. Moreover, it has been generally accepted that the thermal damage in epoxy matrix CFRP due to fires, lightning strikes, ground-reflected efflux from the engines, accidents, etc. is related to high temperatures of above 200° C. on CFRP.

SUMMARY

In one embodiment of the present disclosure, a method of detecting high-temperature exposure of a composite may include applying a composition comprising an adduct suitable for detecting heat and/or mechanical stress in a composite, wherein the adduct reverts to first and second adduct components after exposure of the composition to a temperature of from about 190° C. to about 260° C. to a surface of the composite; exposing the surface to which the composition has been applied to ultraviolet light; and measuring fluorescence of the composition.

In another embodiment, a method of detecting high temperature exposure of a composite in need thereof may include applying a composition comprising an adduct suitable for detecting heat and/or mechanical stress in a composite, wherein the adduct reverts to first and second adduct components after exposure of the composition to a temperature of from about 190° C. to about 260° C. to a surface of the composite; exposing the surface to which the composition has been applied to ultraviolet light; and measuring fluorescence of the composition.

In yet another embodiment, a method of detecting high-temperature exposure of a composite may include (a) applying a composition comprising an adduct suitable for detecting heat and/or mechanical stress in a composite, wherein the adduct reverts to first and second adduct components after exposure of the composition to a temperature of from about 190° C. to about 260° C. to a surface of a component made of the composite; (b) exposing the surface to which the composition has been applied to ultraviolet light; (c) measuring fluorescence of the composition; and (d) determining exposure to high temperature between steps (a) and (b) by comparing the fluorescence of the composition measured in step (c) to fluorescence of a sample of the composition unexposed to high temperature.

In still another embodiment, a system for detecting a high temperature exposure of a composite, the system may include a) a light source for transmitting light of a first wavelength onto a surface of the composite which surface comprises a composition comprising an adduct suitable for detecting heat and/or mechanical stress in the composite; and b) a detection means for detecting light of a second wavelength as a result of composition fluorescence upon adduct reversion to first and second adduct components after exposure of the composition to heat and/or mechanical stress.

Other objects and advantages of the disclosed composition and method will be apparent from the following description and the appended claims.

DETAILED DESCRIPTION

Figure 3:
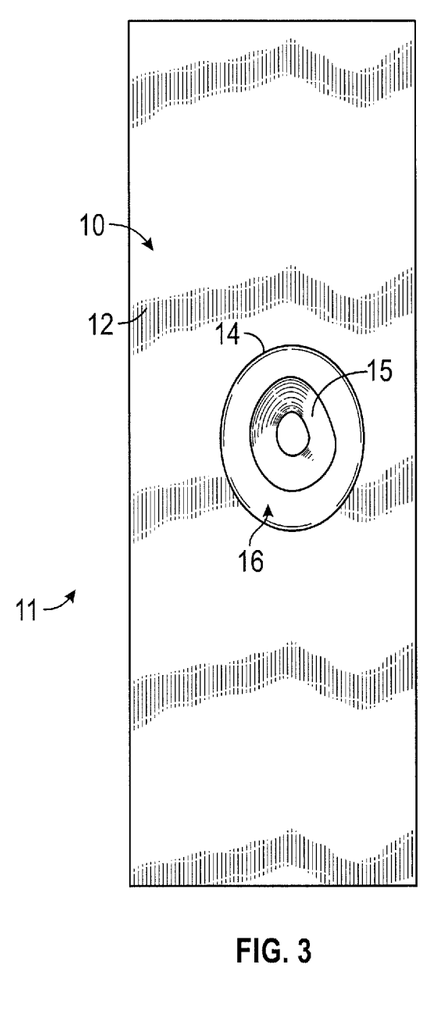
FIG. 3 is a top view of a portion of a composite surface including a heat-damaged region.

As shown in FIG. 3, a region 10 of composite 11, which may by a carbon fiber reinforced plastic (CFRP), may have a surface coating 12 including a composition having a probe, that is, an adduct, suitable for detecting heat and/or mechanical stress in a composite, wherein the adducts reverts to first and second adduct components after exposure of the composition to a high temperature. The surface coating 12 may have a repair area 14 that may include a central damaged region 15. The central damaged region 15 may have been exposed to a high temperature from, for example, a lightning strike. As a result of the exposure to the high temperature, fluorescence of the composition in the surface coating 12 of the central damaged region 15 may be quenched. The central damaged area 15 may represent heating to such a degree that all organic components may be degraded, destroyed, oxidized, and/or carbonized. As a result, the damaged region 15 may be visible to the human eye. In the annular area 16 surrounding central damaged region 15, the damage to the region 10 may or may not be visible to the human eye. However, in the annular area 16 the adduct has, through the high heat, reverted to the first and second adduct components, from which fluorescence may be visible upon excitation with an ultraviolet light source.

The adduct may be selected to revert to first and second adduct components after exposure of the composition to a temperature of from about 190° C. to about 260° C. Certain thermochromatic probes, or adducts, are available for purchase through the company Soluxra, LLC, which can be reached at PO Box 85285 Seattle, Wash. 98145, and on the interne at http://www.soluxra.com. Such probes may be available or sold under code names AJNDE16, AJNDE30, AJNDE31, AJNDE32, AJNDE33, and AJNDE34 (hereinafter probes 16, and 30-34, respectively).

In an embodiment, the composition included in the surface coating 12 may be suitable for incorporation into or on composites comprising a thermochromatic probe may be selected from the group consisting of probes 16, 30, 31, 32, 33, and 34. Probe 34 may be preferred.

In an embodiment, the adduct may revert to the first and second precursors at a temperature from about 200° C. to about 260° C., or from about 200° C. to about 250° C., or from about 200° C. to about 240° C., of from about 200° C. to about 230° C., or from about 200° C. to about 220° C., or from about 200° C. to about 210° C., or from about 220° C. to about 260° C., or from about 220° C. to about 250° C., or from about 220° C. to about 240° C., or from about 220° C. to about 230° C. or from about 230° C. to about 260° C. or from about 230° C. to about 250° C., or from about 230° C. to about 240° C., or from about 240° C. to about 260° C. or from about 240° C. to about 250° C., or from about 250° C. to about 260° C., or from about 260° C. to about 270° C., or from about 270° C. to about 280° C., or from about 280° C. to about 290° C., or from about 290° C. to about 300° C.

In an embodiment, the composition included in the surface coating 12 may fluoresce, after heat or mechanical stress sufficient to cause adduct reversion, at a wavelength of from about 500 to about 800 nm upon treatment with an ultraviolet light excitation wavelength of from about 350 to about 400 nm. In an embodiment, the excitation wavelength may be about 370 to about 400 nm. In an embodiment, the excitation wavelength may be from about 380 to about 400 nm. In an embodiment, the excitation wavelength may be from about 390 to about 400 nm.

In an embodiment, the excitation source may be at electromagnetic radiation wavelength, e.g., from far infrared to far ultraviolet. The wavelengths may include the following typical ranges and/descriptors: Gamma radiation; X-ray radiation; ultraviolet radiation; visible radiation; infrared radiation; and terahertz radiation. For example, such excitation electromagnetic radiation may be far-infrared, e.g., from 300 GHz (1 mm) to 30 THz (10 µm); or mid-infrared, e.g., from 30 to 120 THz (10 to 2.5 µm); or near-infrared, e.g., from 120 to 400 THz (2,500 to 750 nm); or ultraviolet UV e.g., 400-100 nm (3.10-12.4 eV); ultraviolet A UVA e.g., 400-315 nm (3.10-3.94 eV); or Ultraviolet B UVB e.g., 315-280 nm (3.94-4.43 eV); or Ultraviolet C UVC e.g., 280-100 nm (4.43-12.4 eV); or Near Ultraviolet NUV 400-300 nm (3.10-4.13 eV); or Middle Ultraviolet MUV e.g., 300-200 nm (4.13-6.20 eV); or Far Ultraviolet FUV, e.g., 200-122 nm (6.20-10.16 eV); or Hydrogen Lyman-alpha H Lyman-α e.g., 122-121 nm (10.16-10.25 eV); or Extreme Ultraviolet EUV, e.g., 121-10 nm (10.25-124 eV); or Vacuum Ultraviolet VUV e.g., 200-10 nm (6.20-124 eV).

In an embodiment, the composition included in the surface coating 12 typically may be a viscous liquid, suitable to be painted on, brushed on, sprayed on, or by other means known to a person of ordinary skill in the art, applied on the surface of a composite material. In an embodiment of the present disclosure, the composition may comprise a basic, nonaqueous solvent, such as a polyamine, the polyamine being optionally alkylated. In an embodiment of the present disclosure, the composition also may comprise an ether of bisphenol, e.g. bisphenol A.

In an embodiment, the probe, or adduct, may be incorporated, or by other means known to a person of ordinary skill in the art, admixed in, or incorporated into a repair epoxy composition (not shown) suitable for repair of CFRP. In an embodiment of the present disclosure, the probe may be incorporated in the composite 10 made of CFRP. In an embodiment, the composition may be applied to, or may further comprise, a composite.

In an embodiment, the composition may include very small amounts of the probe. For example, the composition may comprise, in a typical amount, from 0.001% to 3%, or from 0.001% to 2% or from 0.001% to 1% or from 0.01% to 3% or from 0.01% to 2% or from 0.01% to 1% or from 0.1% to 3%, or from 0.1% to 2% or from 0.1% to 1%, or from 0.1% to 0.8% or from 0.2% to 0.8%, or from 0.3% to 0.7%, or from 0.4% to 0.6%, or about 0.5% of the probe by weight of composition.

In an embodiment, the disclosed method of detecting high-temperature exposure of a composite may include applying the composition of the present disclosure to a surface of the composite, exposing the surface to the which the composition has been applied to ultraviolet light, and measuring fluorescence of the composition.

In an embodiment, a method of detecting high temperature exposure of a composite in need thereof may include applying the composition of the present disclosure to the surface of the composite, exposing the surface to which the composition has been applied to ultraviolet light, and measuring fluorescence of the composition.

In an embodiment, fluorescence intensity and/or the ultraviolet-visible absorption of the composition may decrease over time. The decrease may be related to the exposure of the composition to air, and the concentration of oxygen in the air. For example, in an embodiment of the present disclosure, fluorescence of the composition may be substantially quenched after about an hour (60 minutes) or greater of exposure to a temperature of about 200° C. or greater; and/or after about 30 to 45 minutes of exposure to a temperature of about 230° C.; and/or after about 15 to 25 minutes of exposure to a temperature of about 260° C. With an understanding of the time and temperature relationship that the fluorescence of a particular probe may be substantially quenched, the person of ordinary skill in the art may have an analytical technique by which to estimate the probability of exposure to composite-damaging high temperatures.

In an embodiment, the normalized absorbance ($A/A_{max}$) of the composition may be substantially reduced to a value of from 0.01 to 0.1 after about 180 minutes or greater of exposure to a temperature of about 200° C. or greater; and/or the normalized absorbance of the composition may be substantially reduced to a value of from 0.01 to 0.2 after about 60 to 90 minutes of exposure to a temperature of about 230° C.; and/or the normalized absorbance of the composition may be substantially reduced to a value of from 0.01 to 0.1 after about 30 minutes or greater of exposure to a temperature of about 260° C. The decrease may be related to the exposure of the composition to air, and the concentration of oxygen in the air. With an understanding of the time and temperature relationship that the normalized absorbance ($A/A_{max}$) of a particular probe may be substantially decreased, the person of ordinary skill in the art may have an analytical technique by which to estimate the probability of exposure to composite-damaging high temperatures.

Figure 4:
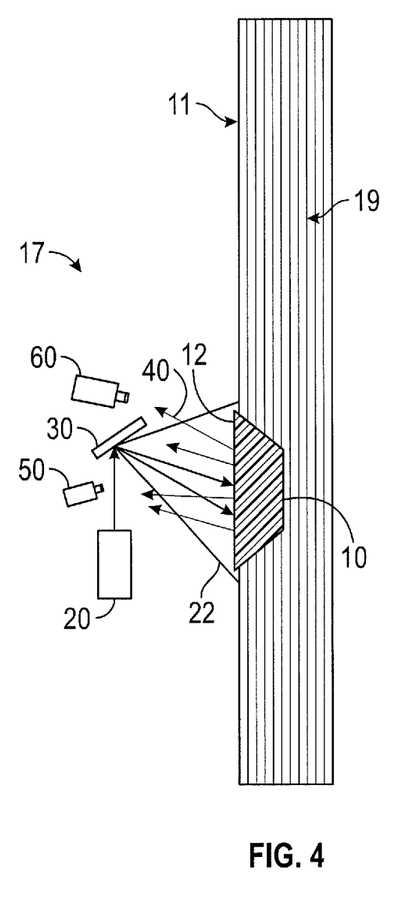
FIG. 4. is a schematic side view of an embodiment of the disclosed system for detecting a heat-damaged composite.
Figure 5:
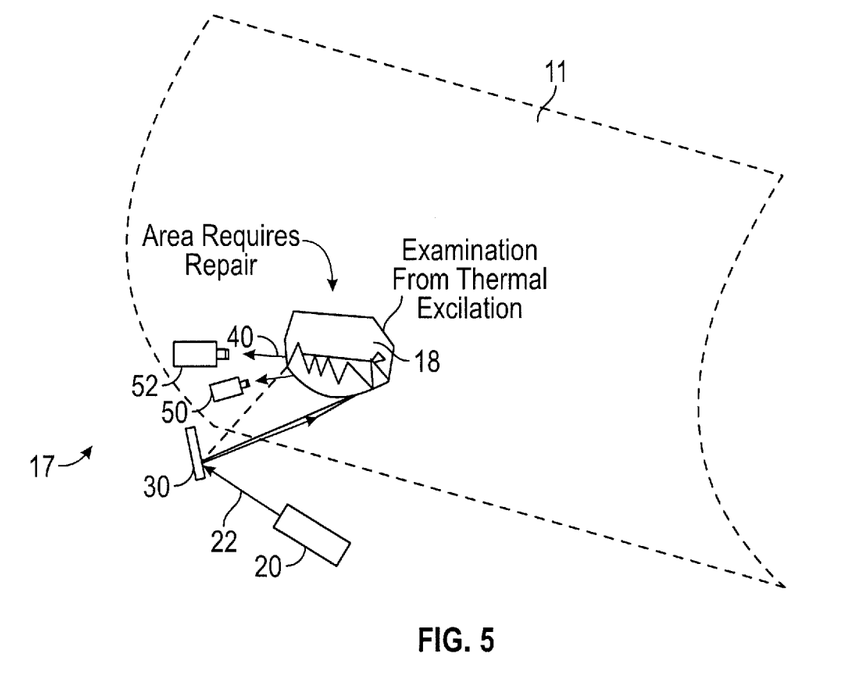
FIG. 5. is a schematic oblique view of another embodiment of the disclosed system 4 for detecting a heat-damaged composite.

As shown in FIGS. 4 and 5, in an embodiment of the disclosed system, generally designated 17, the surface 12 of the region 10 of composite 11, which may represent a portion of a larger composite structure 19, for example, an aircraft fuselage, may be irradiated with ultraviolet light 22, emitted by an excitation source 20, for example a laser, after being reflected onto a composite surface window 18 by mirror 30. Window 18 may be a region of the larger composite structure 11, and may or may not be coextensive with the region 10. Typically, the window 18 may be of greater surface area than region 10, as part of a method to systematically scan a composite 11 by gridded region.

The composition may emit light 40 that is detected by a detection means, which in the system 17 may be in the form of a visible light camera 50, an infrared light camera 52 (see FIG. 5), and/or a multi-filter imager 60 (see FIG. 4). In embodiments, the imager 60 may be one or more of a high-speed gated intensifying camera, a photomultiplier tube, and/or a single line spectrometer.

Figure 6:
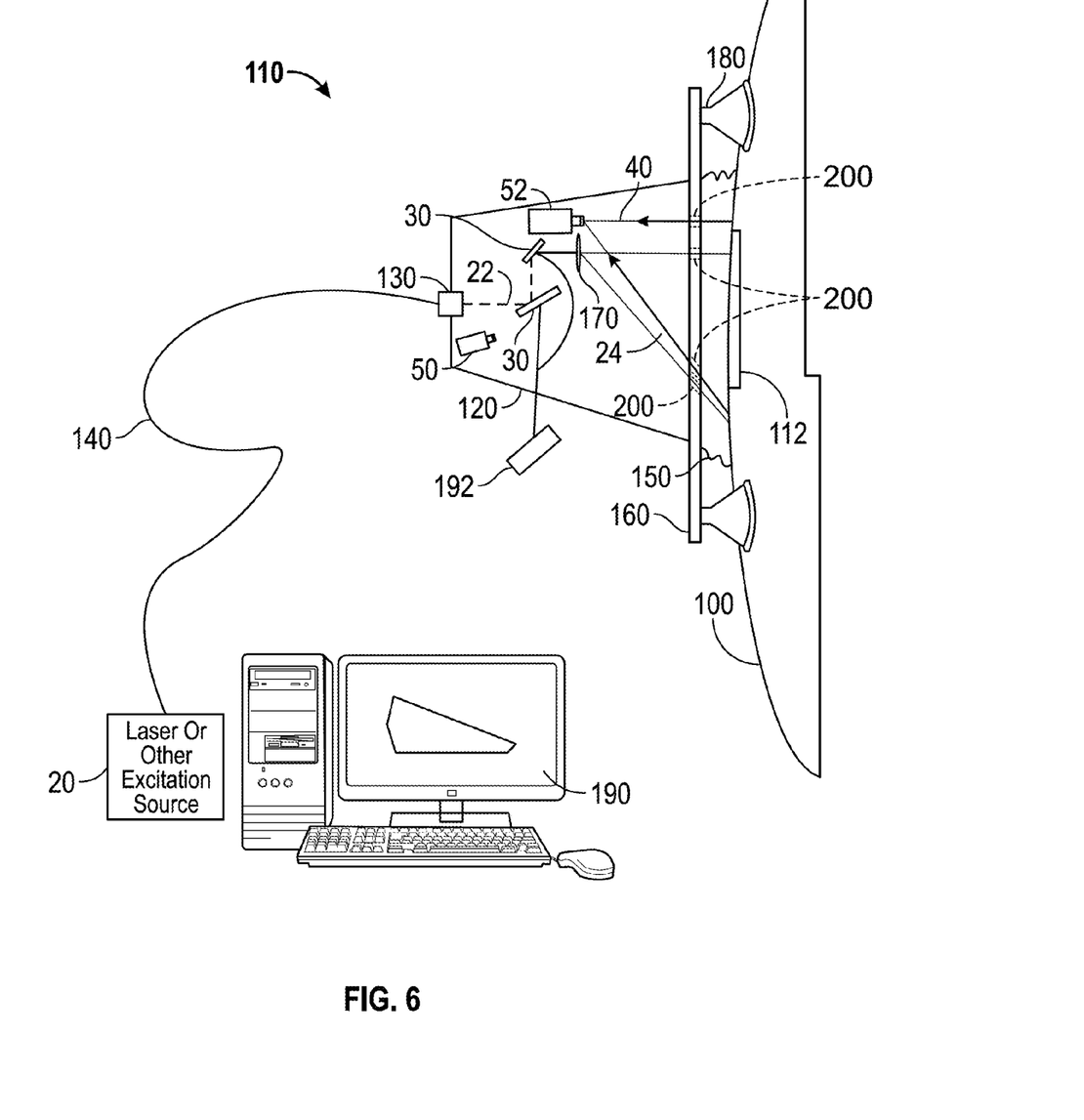
FIG. 6 is a schematic representation of yet another embodiment of the disclosed system for detecting a heat-damaged composite.

As shown in FIG. 6, in an embodiment, a system, generally designated 110, may be used to detect a repair area 112 that may have been damaged by exposure to high temperature, for example, by a lightning strike. The repair area 112 may be a part of a larger structure 100, such as a fuselage structure. The fuselage structure 100 may be scanned by the system 110. System 110 may include a hood 120, inside of and onto which is mounted an ultraviolet light emission source 130 that may be operably connected to excitation source 20, which in an embodiment may be a laser, by a fiber optic link 140 such that the ultraviolet light may be emitted from a source 130 onto the surface 150 of fuselage 100.

A visible light camera 50 and/or infrared light camera 52 may be mounted on or inside the hood 120. Ultraviolet light 22 may be directed from the source 130 onto the surface 150 via mirrors 30, which also may be mounted on or inside of the hood 120. Light 40 may fluoresce from surface 150 and may be detected by cameras 50 and/or 52. The hood 120 may be mounted on the surface 150 by mounting plate 160. Mounting plate 160 may include one or more apertures 200 through which ultraviolet light 22 may be directed onto surface 150 and/or through which fluorescing light 40 may pass to be detected by cameras 50 and/or 52. Mounting plate 160 may be reversibly mounted to surface 150 by any reversible mounting means known to a person of ordinary skill in the art, for example suction cups 180.

In another embodiment, and with respect to FIG. 6, light 22 may be scattered through an aperture 170, mounted on or inside of hood 120, to provide a light cone 24 that is directed onto the surface 150. In another embodiment, light 22 may be focused onto the surface 150 by the aperture 170 and/or by a collimator, both of which may be mounted on or inside hood 120, both of which are known to a person of ordinary skill in the art.

In another embodiment, cameras 50 and/or 52 and/or multi-filter imager 60 may be operatively connected to a controller 190. Controller 190 may include a computer that includes software and memory for the purpose of controlling the operation of system 110. Controller 190 may be operably linked to excitation source 20 to control emission of ultraviolet light in coordination with the control of system 110. The controller may be capable of automating ultraviolet emission and/or fluorescence detection, and/or execute software and/or hardware routines to systematically scan surface 150. Controller 190 may also include software and or hardware to provide an image or images of surface 150.

In an embodiment, the excitation light 22 may be controlled by an excitation beam steering mechanism 192, which may control mirrors 30, which may be in the form of a multiple-optical mirror with rotating prism. The excitation beam steering mechanism 192 may be configured to direct light of a first wavelength onto one or more predetermined areas on the surface of the composite by the controller 190.

The following non-limiting examples illustrate the invention.

Example 1

Hysol EA 9390 Part A (epoxy resin) and part B (curing agent) were mixed by hand in a ratio of 100:56 parts by weight to form a neat epoxy. Both Part A and Part B were made by Henkel Corporation and used as-received. Probe 16 was added to another batch of epoxy to provide a 0.05 wt % probe in epoxy, with the same mixing ratio of resin to curing agent as the neat epoxy, hereafter called "probe doped epoxy." Small portion of both resins were spin coated onto glass substrates at speeds between 3500 and 4000 rpm to form thin films. The films were then cured at 121° C. (250° F.) for 2.5 hours in a Thermo Scientific Heratherm Advanced Protocol mechanical convection oven.

The remaining epoxy from both the neat epoxy and blank was used to wet-layup composite panels with 3 plies of T800 plain weave carbon fiber fabric (Toray). After the wet lay-up the composite panels were processed by conventional vacuum bag process and cured in an autoclave at 121° C. (250° F.) for 2.5 hours.

The thin films of neat epoxy and the probe doped epoxy were subjected to heat-treatments at temperatures of 204° C. (400° F.), 232° C. (450° F.), and 260° C. (500° F.) in the convection oven. The films were removed from the oven at certain intervals to measure the fluorescence and UV-Visible absorption spectra. After the measurements were made the thin-films were placed back into the oven at the same temperature and this process was repeated until the fluorescence of the sample was no longer distinguishable from the noise in the baseline.

Fluorescence measurements were made on a Stellarnet BlueWave UVN spectrometer with a R600-8-UVVIS SR reflectance probe. The probe contained a 600 μm read fiber (detector) at the core and is surrounded by 7 fibers that focus the excitation source onto the sample. A blue 470 nm LED was used as the excitation source for the fluorescence measurements. The probe was at a 45° angle to the surface of the sample and the bottom portion of the probe rested on surface of the sample to try to reduce the effects of variations in the thickness of the samples on the distance to probe. The integration time for the detector was set to 2000 ms and 9 scans of each spectrum were averaged. Samples were cooled to room temperature after heat-treatment before the fluorescence spectra were measured.

UV-Vis spectra of the thin films of both the neat epoxy and the probe doped epoxy were measured from 250 to 900 nm at a scan rate of 240 nm/min using a Thermo Scientific Evolution 300. An uncoated glass substrate was used as the reference. Samples had been cooled to room temperature after heat-treatments before the spectra were measured.

After exposure to 250° C. for 2 minutes, probe 16 did not show any change. When the sample was isothermally treated at a longer time, for example, 5 min and 10 min, a fluorescence peak around 433 nm gradually increased, consistent with thermal generation of a longer-wavelength probe 16 precursor. After isothermal treatment of the sample at 250° C. for 20 min, most of probe 16 had been converted to the precursor. Furthermore, at the higher temperatures of 255° C. and 260° C., the conversion to the probe precursor can be accelerated significantly This study clearly showed that the probe met the required operational temperature window.

Figure 1A:
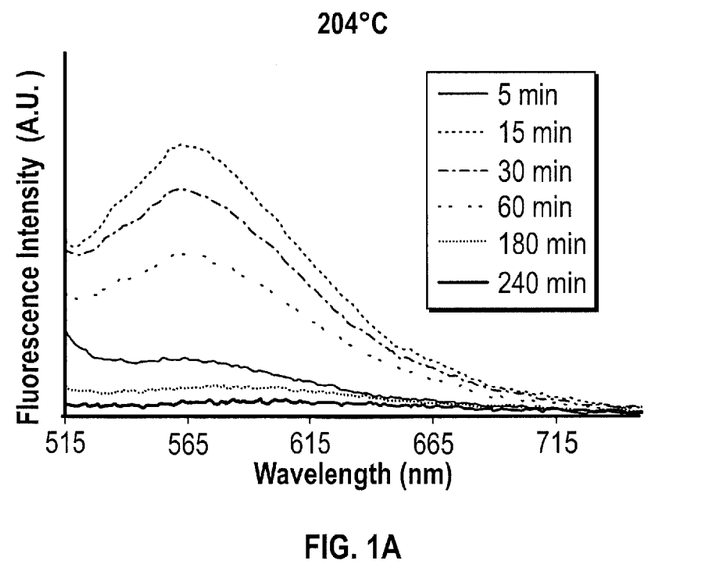
FIGS. 1a, 1b, and 1c are graphs of the fluorescence spectrum over time of the disclosed probe 16-doped epoxy samples, heat-treated for several exposure times.
Figure 1B:
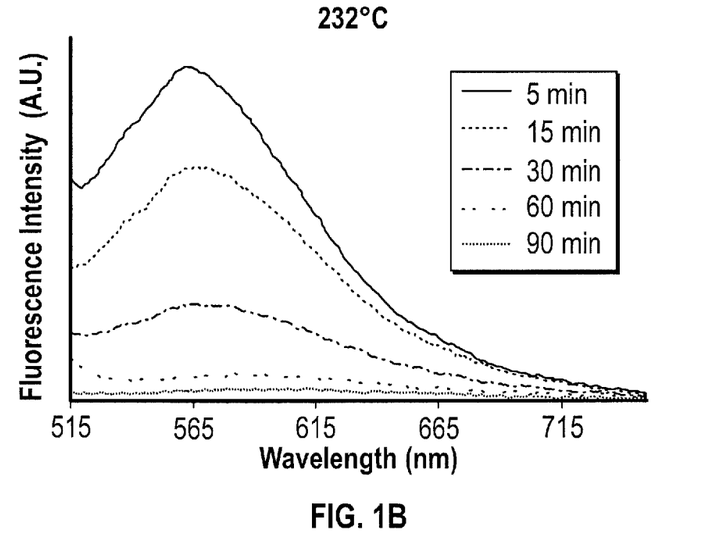
Figure 1C:
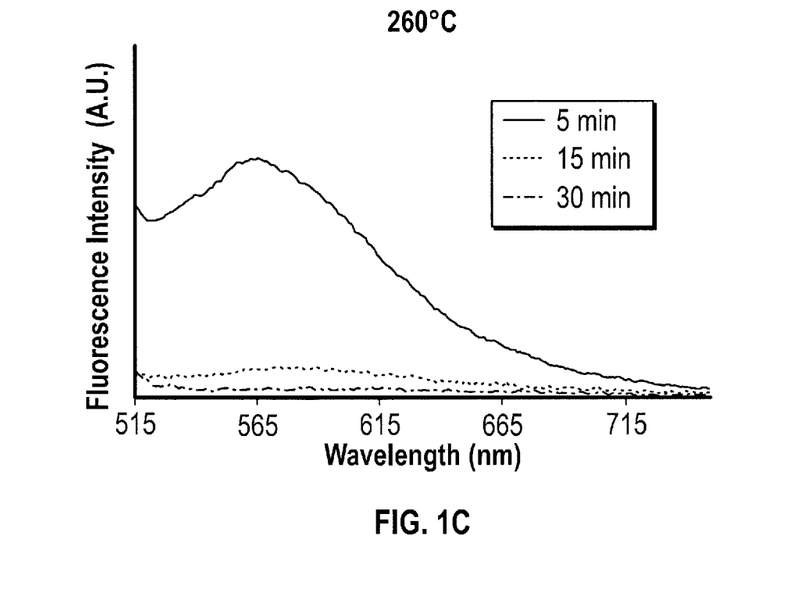

The samples treated at 232° C. and 260° C. exhibited maximum fluorescence intensity after 5 minutes of exposure time. However, in the case of thermal treatment at 204° C., it can be seen in FIG. 1 that the dye reached maximum intensity after 15 min, indicating that the kinetics of activation of probe 16 were slower at the lower temperature. It should be noted from the kinetics study on probe 16, however, that the activation of the probe in the epoxy samples occurred considerably faster than expected at 204° C. and 232° C. The cause of this change in kinetics in the matrix is still under investigation. It can also be seen that after prolonged exposure to all of the heat-treatment temperatures, the intensity of the fluorescence emission decreased to a level where it could no longer be observed. At the same time, the wavelength of maximum intensity λmax also exhibited a bathochromic shift. These phenomena have also been observed in CFRP when using LIF. The rate at which these changes to the fluorescence spectrum occurred was also strongly dependent on the heat-treatment temperature. At 260° C. the fluorescence was no longer observed after 30 minutes, while it took 240 min for the same thing to occur at 204° C. Even though the fluorescence emission becomes harder to see with long exposure times to the point where it cannot be observed visually, this result may not be detrimental to this inspection method. Most thermally damaged parts have a thermal damage gradient surrounding the damage site where the fluorescence may still be visible. In that case, the quenched fluorescence emission can actually be very useful because it indicates an area where severe thermal damage has occurred.

Figure 2A:
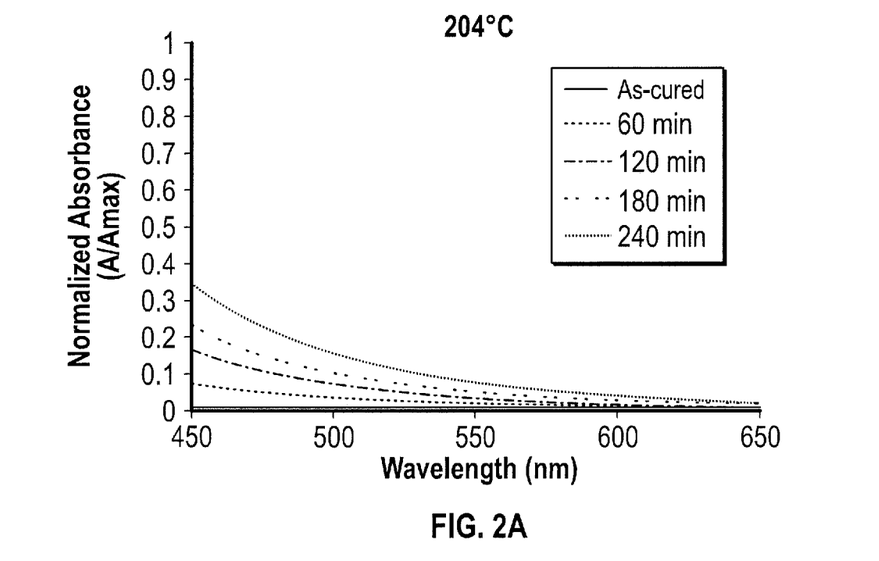
FIGS. 2a, 2b and 2c are graphs of UV-VIS absorption spectra of the disclosed probe 16-doped epoxies, heat-treated for several exposure times.
Figure 2B:
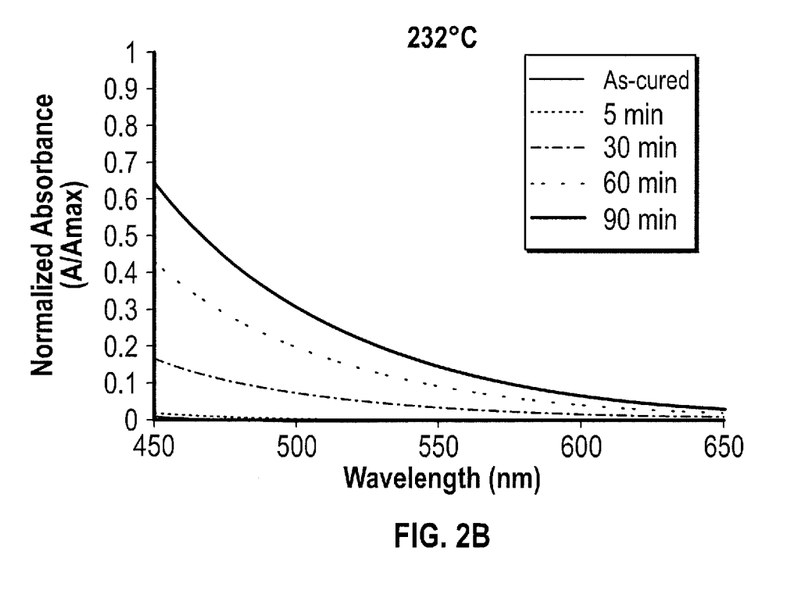
Figure 2C:
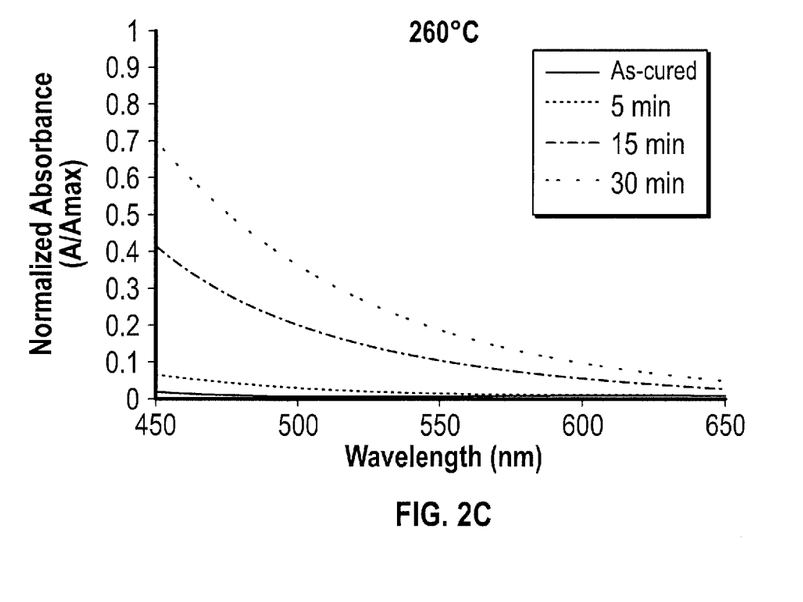

A potential explanation for the change in the fluorescence emission intensity and wavelength as a function of exposure time and temperature can be found by examining the UV-VIS absorption spectra seen in FIG. 2. The absorbance of each spectrum was normalized relative to its maximum absorbance Amax to account for small variations in the thickness of the films. The absorbance of the thin-films of the probe doped epoxy was too high for the detector to record any values at wavelengths in the UV-range so those spectra could not be normalized. It was found during testing that the decay of the absorption at wavelengths below the maximum absorbance was found to be almost identical to that of the neat epoxy exposed to the same heat-treatment so it is possible to analyze the behavior of the probe doped epoxy in the wavelength range of interest using the UV-Vis spectra from the neat epoxy.

Example 2

Probe 34 is dissolved into diethylenetriamine, and diluted with Bisphenol A, diglyme ether to provide a 0.5% solution of the probe. After one hour in high vacuum the resulting viscous resin is painted onto a composite to provide 100 cm$^2$ of treated surface. The composite is cured at 170° C. Then, a 4 cm$^2$ area is rapidly heated to 240° C. and fluorescence measured every minute for twenty minutes, the fluorescence induced by a 395 nm ultraviolet light source. In an area where no heat is applied, fluorescence is found at less than 500 nm, and in an area exposed to at a temperature of 240° C., fluorescence is found at 550 nm to 750 nm, peaking around 575-625 nm.

Example 3

Thermochromatic probe 34 is added to: a) resin in the repair pre-preg or pre-cured doubler surface ply; b) adhesive used for bonded or scarfed repairs; c) the primer, top coat or surface ply resin system on an aircraft surface. This third option is obviously done during manufacturing, though the coating can be done during re-paint.

During the repair, the appropriate light (UV, IR, etc.) may be shone over the exposed surrounding areas surface to check for fluorescent shifts (changes in color or a turning on or off of fluorescence), thereby monitoring the area for signs of over-heating or out-of-spec heating. Fluorescence of coatings or resins on or in materials that have been subjected to an over-heat condition will have a different signature than other structure. Out-of-spec indications may indicate to a technician that his/her process must be stopped, and changes then may be made to the heat blankets, heat sinks, etc. before continuing. Once the changes are made, the curing is re-started and monitoring continues until the cure is complete.

Once the cure is done, the bagging material is removed, and a quick check using this same process may verify that none of the surrounding area that was under the bag, or the repair itself is thermally damaged. If any area is indicated to have experienced some over-heating, fluorescent images may be produced using a camera, while the appropriate light, or excitation source, may be applied to the area. The fluorescent images can be used for MRB assessment in a general way, or as input to a FEM, changing the local properties based upon the data. Either way, the witness information may be used by MRB to predict the performance of the repair or surrounding area, and validate the area has sufficient properties, or determine if a repair is needed.

The adhesive that is exposed around the edge of the repair also may be checked in a similar manner to verify sufficient and uniform temperatures were reached to ensure sufficient properties are met. The repair itself may be covered with a thermochromatic coating that can prove for a rapid pre-NDI if thermal damage due to lightning strike or exhaust or fire occurs during in-service. The repair may be inspected and released.

While the compositions and methods described herein constitute preferred embodiments of the disclosed invention, it is to be understood that the invention is not limited to these precise compositions and methods, and that variations may be made therein without departing from the scope of the invention.

What is claimed is:

1. A system, comprising:
    a composite having a surface;
    an excitation source for transmitting light of a first wavelength onto the surface of the composite, the surface including a repair composition having an adduct that detects heat in the composite;
    a mounting plate defining at least one aperture for the passage of light;
    a hood mountable upon the surface of the composite by the mounting plate, wherein the hood includes an inside portion;
    a detector positioned within the inside portion of the hood, wherein the detector receives a fluorescence generated by the adduct indicating one of an over-heating and an out-of-spec heating condition of the repair composition; and
    a controller in communication with the detector to receive the fluorescence detected by the detector, wherein the controller determines if the repair composition experiences at least one of the over-heating and the out-of-spec heating condition based on the fluorescence generated by the adduct during curing of the repair composition.

2. The system of claim 1, wherein the excitation source is a source of ultraviolet light.

3. The system of claim 1, wherein the excitation source is a laser.

4. The system of claim 1, wherein the detector is one or more of a visible light camera, an infrared light camera, and a multi-filter imager.

5. The system according to claim 4, wherein the multi-filter imager is one or more of a high-speed gated intensifying camera, a photomultiplier tube, and a single line spectrometer.

6. The system of claim 1, further comprising an excitation beam steering mechanism configured to direct the light of the first wavelength onto one or more predetermined areas on the surface of the composite.

7. The system of claim 1, wherein the controller automates fluorescence detection by the detector, and executes software and hardware routines to systematically scan the surface of the composite.

8. The system of claim 1, wherein the controller actuates the excitation source to control emission of the light of the first wavelength.

9. The system of claim 1, wherein the adduct reverts to first and second adduct components after exposure to a predefined range of temperatures.

10. The system of claim 1, wherein the fluorescence of the adduct generates a distinct signature to indicate the over-heating and the out-of-spec heating condition of the repair composition.

11. A method of repairing a composite material having a damaged region, the method comprising:
    applying a repair composition to the damaged region of the composite material, wherein the repair composition includes an adduct incorporated therein and the adduct detects heat in the composite material;
    providing a system including an excitation source for transmitting light of a first wavelength onto the damaged region of the composite material, a mounting plate defining at least one aperture for the passage of light, a hood mountable upon the composite material by the mounting plate including an inside portion, a detector positioned within the inside portion of the hood that receives a fluorescence generated by the adduct indicating one of an over-heating and an out-of-spec heating condition of the repair composition, and a controller in communication with the detector to receive the fluorescence detected by the detector;
    exposing the composite material and the damaged region to the light of the first wavelength to cause the adduct to generate a fluorescence indicating one of the over-heating and the out-of-spec heating condition of the repair composition;
    measuring the fluorescence of the composite material and the damaged region; and
    determining, by the controller, if the repair composition experiences at least one of the over-heating and the out-of-spec heating condition based on the fluorescence generated by the adduct during curing of the repair composition.

12. The method of claim 11, wherein the adduct is added as one of: a resin in a repair pre-preg, a resin in a pre-cured doubler surface ply, an adhesive for bonded repairs, and an adhesive for scarfed repairs.

13. The method of claim 11, wherein the fluorescence of the adduct generates a distinct signature to indicate the over-heating and the out-of-spec heating condition of the repair composition.

14. The method of claim 11, wherein the composite material is part of an aircraft fuselage.

15. The method of claim 11, wherein the specified light is ultraviolet light.

16. The method of claim 11, wherein the adduct reverts to first and second adduct components after exposure to a predefined range of temperatures.

17. The method of claim 12, wherein the predefined range of temperatures range from about 190° C. to about 260° C.

18. The method of claim 11, wherein the detection device is selected from the group consisting of at least one of a: a visible light camera, an infrared camera, and a multi-filter imager.

19. The method of claim 11, comprising executing software and hardware routines to systematically scan a surface of the composite material by the controller.

* * * * *

UNITED STATES PATENT AND TRADEMARK OFFICE
CERTIFICATE OF CORRECTION

PATENT NO.       : 9,372,177 B2  
APPLICATION NO.  : 13/840980  
DATED            : June 21, 2016  
INVENTOR(S)      : Gary E. Georgeson, Megan N. Watson and Morteza Safai Page 1 of 1

It is certified that error appears in the above-identified patent and that said Letters Patent is hereby corrected as shown below:

Claims

In Column 10, Line 53, Claim 17 reads "17. The method of claim 12,"

It should read:

-- 17. The method of claim 16, --

Signed and Sealed this
Twenty-third Day of August, 2016

Michelle K. Lee
*Director of the United States Patent and Trademark Office*